United States Patent
Poole

(10) Patent No.: US 6,865,940 B2
(45) Date of Patent: Mar. 15, 2005

(54) ALUMINUM OXIDE MOISTURE SENSOR AND RELATED METHOD

(75) Inventor: John McKinley Poole, Maynard, MA (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 10/604,080

(22) Filed: Jun. 25, 2003

(65) Prior Publication Data

US 2004/0261526 A1 Dec. 30, 2004

(51) Int. Cl.[7] .............................................. G01N 19/00
(52) U.S. Cl. .................................. 73/335.05; 73/29.01
(58) Field of Search ................................ 73/1.01, 1.02, 73/1.06, 1.07, 29.01, 29.02, 29.05, 335.02, 335.03, 335.04, 335.05

(56) References Cited

U.S. PATENT DOCUMENTS

| | | | |
|---|---|---|---|
| 3,983,527 A | * 9/1976 | Ohsato et al. ................. 338/35 |
| 4,057,823 A | 11/1977 | Burkhardt et al. | |
| 4,080,564 A | * 3/1978 | Nitta et al. .................. 324/703 |
| 4,144,636 A | 3/1979 | Burkhardt et al. | |
| 4,217,623 A | 8/1980 | Nishino et al. | |
| 4,263,576 A | * 4/1981 | Murata et al. ................. 338/35 |
| 4,549,134 A | 10/1985 | Weiss | |
| 4,655,076 A | 4/1987 | Weihe et al. | |
| 4,793,182 A | 12/1988 | Djorup | |
| 5,040,411 A | 8/1991 | Medzius | |
| 5,198,771 A | * 3/1993 | Fidler et al. ................. 324/438 |
| 5,347,468 A | * 9/1994 | Rupp et al. .................. 700/284 |
| 5,792,938 A | * 8/1998 | Gokhfeld .................... 73/29.02 |
| 5,801,307 A | * 9/1998 | Netzer ..................... 73/170.17 |
| 5,985,673 A | * 11/1999 | Bao et al. .................... 436/151 |
| 6,437,322 B1 | * 8/2002 | Teder ..................... 250/227.25 |
| 6,564,633 B2 | * 5/2003 | Stormbom ................ 73/335.05 |
| 6,615,150 B1 | * 9/2003 | Nelson et al. ................. 702/85 |
| 6,653,964 B2 | * 11/2003 | Mizuno et al. .............. 341/155 |
| 2004/0045824 A1 | * 3/2004 | Hada et al. .................. 204/425 |

FOREIGN PATENT DOCUMENTS

CA     2345631 A1 * 11/2001     ........... D06F/58/28

OTHER PUBLICATIONS

"Principles of Moisture Measurement," by E.J. Rosa, Ph.D. (undated).
"Air Dry Advanced Aluminum Oxide Sensor," Joslyn Sunbank Company, LLC.
"Comparison of Moisture Sensors, Ver. 1.0," Process Improvements Solutions, Inc., 1997.
"8800 Series—Trace Moisture Analysis Instrumentation," Teledyne Analytical Instruments, 2000.

* cited by examiner

Primary Examiner—Charles D. Garber
(74) Attorney, Agent, or Firm—Nixon & Vanderhye P.C.

(57) ABSTRACT

A method of operating an aluminum oxide moisture sensor to measure moisture in a sample gas, where the sensor comprises a pair of electrodes sandwiched about a dielectric, the method comprising: a) heating the sensor to a first temperature above the sample gas temperature and holding the sensor at said first temperature for a first predetermined period of time; b) cooling down the sensor to a second lower temperature over a second predetermined period of time; c) taking plural samples of sensor conductance over a third predetermined period of time at the lower temperature; and d) determining a rate of adsorption of the moisture and using the rate of adsorption as a measure of moisture in the sample gas.

22 Claims, 2 Drawing Sheets

ALUMINUM OXIDE MOISTURE SENSOR AND RELATED METHOD

BACKGROUND OF INVENTION

This invention relates to moisture sensors and more specifically, to a manner of using an aluminum oxide moisture sensor that improves the speed of response of the sensor.

An aluminum oxide moisture sensor (or hygrometer) uses aluminum oxide and a thin film of noble metal to form what is essentially a capacitor. The water molecules in the test medium are absorbed and electrical impedance is measured. The capacitor's value is then translated and displayed as a value of, for example, PPM.

More specifically, a typical aluminum oxide sensor is comprised of an aluminum base that is anodized to produce a thin layer of active aluminum oxide. A thin coating of noble metal, for example, gold, is evaporated over this structure, and the two metal layers form the electrodes of the capacitor, while the aluminum oxide serves as the dielectric, sandwiched between the electrodes.

When the sensor is exposed to moisture, water vapor is rapidly transported through the exposed (positive) electrode layer where the polar water molecules form weak hydrogen bonds at the oxide surfaces. Adsorption causes changes in the dielectric constant and resistivity of the oxide layers. Thus, a measure of the sensor conductance is a measure of moisture loading on the aluminum oxide dielectric and is proportional to the moisture concentration in the sample gas.

Activated aluminum oxide is widely used as the dielectric since its adsorption capacity or loading is a function of humidity level of the surrounding gas, temperature, and the oxide layer's thickness and porosity (exposed surface area). These factors will also determine the rate of adsorption.

The properties of hygroscopic sensor materials usually exhibit large temperature dependence. To minimize this effect, sensors often are bonded to an additional substrate containing a heater and RTD assembly for stable temperature control.

It is well known, however, that aluminum oxide moisture sensors exhibit very slow response at trace (PPBV) moisture levels. In addition, measurement methods currently in use rely on equilibrium values, which require several hours to reach. Over time, these measurements also show considerable offset drift, requiring frequent recalibration of the sensors. Past efforts to improve performance have used special algorithms to anticipate sensor response. This method relies on hard-to-measure variables, however, that may vary widely between applications. Without good knowledge of application properties, this factor greatly limits sensor performance.

SUMMARY OF INVENTION

This invention proposes an economical new method of operating an aluminum oxide moisture sensor that reduces drift and dramatically increases the speed of response, but does not require the use of predictive algorithms.

More specifically, this invention takes advantage of the sensor's built-in temperature control by periodically applying a drying cycle to the sensor. This forces the sensor to operate in a region where the sensitivity and rate of adsorption are high. Any variation in the adsorption rate will be due solely to changes in sample moisture concentration.

In the exemplary embodiment, the sensor is heated to well above the sample gas temperature and held for a short period, thus drying the sensor below the gas concentration. After a delay for allowing the sensor temperature to cool down and stabilize, measurements are conducted at the lower temperature only. This minimizes the effects of typically large sensor temperature coefficients. The length of time required for cool-down will vary inversely with the sample flow rate.

During the measurement period, the adsorption rate is determined by:

(1) taking 100 samples of sensor conductance; (2) applying a 10 point moving average filter for noise reduction; and (3) performing a linear regression on the unfiltered data, with the resulting slope (adsorption rate) used as a measure of sample moisture. This method effectively filters any low frequency drift components, increasing measurement accuracy and speed of response.

For sensors that have no heater or other means of temperature control, or if operation of the sensor at high temperatures is undesirable, other drying methods may be used. For example, a source of gas with a moisture content <1 $PPB_v$ may be used to dry the sensor. Alternatively, a Peltier device may be used in place of a heater.

Accordingly, in one aspect, the present invention relates to method of operating an aluminum oxide moisture sensor to measure moisture in a sample gas, where the sensor comprises a pair of electrodes sandwiched about a dielectric, the method comprising: a) heating the sensor to a first temperature above the sample gas temperature and holding the sensor at said first temperature for a first predetermined period of time; b) cooling down the sensor to a second lower temperature over a second predetermined period of time; c) taking plural samples of sensor conductance over a third predetermined period of time at the lower temperature; and d) determining a rate of adsorption of the moisture and using the rate of adsorption as a measure of moisture in the sample gas.

In another aspect, the invention relates to method of operating an aluminum oxide moisture sensor to measure moisture in a sample gas, where the sensor comprises a pair of electrodes sandwiched about a dielectric, and the method comprising: a) heating the sensor to a first temperature above the sample gas temperature and holding the sensor at said first temperature for a first predetermined period of time; b) cooling down the sensor to a second lower temperature over a second predetermined period of time; c) taking plural samples of sensor conductance over a third predetermined period of time at the second lower temperature; and d) determining a rate of adsorption of the moisture and using the rate of adsorption as a measure of moisture in the sample gas; wherein step c) is carried out by taking about 100 samples of sensor conductance, and wherein the third predetermined period of time is about 60 and 90 seconds; and wherein step d) is carried out in part by applying a 10-point moving average filter to the plural samples of sensor conductance to obtain data filtered for noise reduction; and by performing a linear regression on the data filtered for noise reduction to obtain a slope representative of the rate of adsorption.

In still another aspect, the invention relates to a method of operating an aluminum oxide moisture sensor to measure moisture in a sample gas, where the sensor comprises a pair of electrodes sandwiched about a dielectric, the method comprising: a) drying the sensor during a first predetermined period of time to a moisture content level below the moisture content level of the sample gas; b) taking plural samples of sensor conductance over a second predetermined period of time at a temperature of about 35 Å° C. to about 45 Å° C.;

and c) determining a rate of adsorption of the moisture and using the rate of adsorption as a measure of moisture in the sample gas.

The invention will now be described in detail in connection with the following figures identified below.

DETAILED DESCRIPTION

Figure 1:
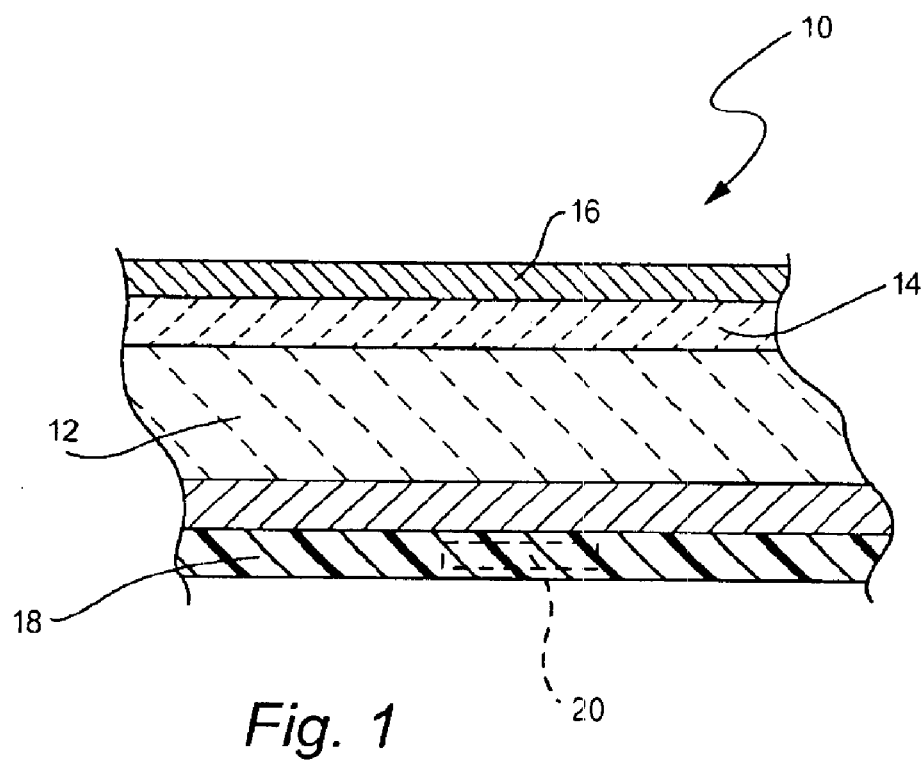
FIG. 1 is a cross section through a conventional aluminum oxide moisture sensor.

FIG. 1 illustrates in a simplified manner (not to scale) the basic structure of an aluminum oxide moisture sensor 10. Typically, the sensor includes an aluminum base 12, the surface of which is anodized to produce a thin layer or film 14 of porous, active aluminum oxide. A thin coating 16 of a noble metal such as gold, is applied (for example, by evaporation) over the layer 14 so that base 12 and coating 16 serve as electrodes of the capacitor, sandwiched about the aluminum oxide dielectric layer 14. The sensor may be bonded to a substrate 18 incorporating a heater 20 that has previously been used to insure a more or less constant sensor temperature.

When the sensor 10 is exposed to moisture, water vapor is transported through the noble metal layer or coating 16 (the positive electrode) and adsorbs onto the dielectric layer 14 by reason of the polar water molecules forming weak hydrogen bonds at the dielectric layer interface. This adsorption causes changes in the dielectric constant and resistivity of the oxide layer. This means that a measure of sensor conductance is a measure of moisture loading on the aluminum oxide, and is proportional to the moisture concentration in the sample gas.

In accordance with this invention, the heater 20 normally used to stabilize the sensor is utilized in a new methodology designed to increase sensor response time.

Figure 2:
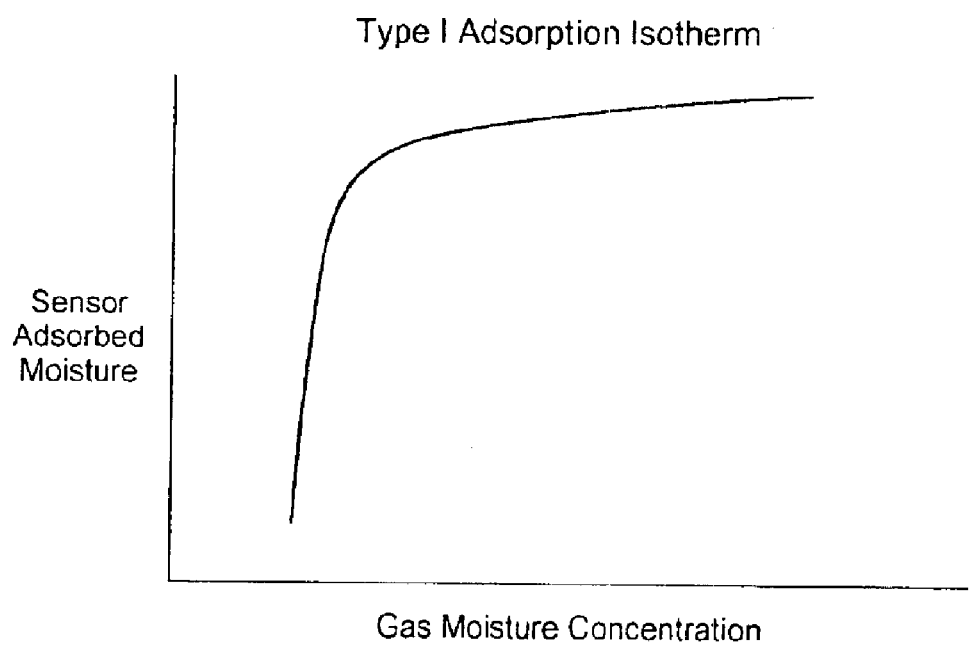
FIG. 2 is a graph showing a known Type-1 or Langmuir Isotherm.

More specifically, and with reference to FIG. 2, a Type-1 or Langmuir Isotherm is shown, and provides the basis for adsorption models of various materials at low moisture concentrations. It predicts that as moisture concentration increases, the rate of adsorption decreases, as fewer sites are available for adsorption. The isotherm eventually reaches some equilibrium value when a maximum number of sites are filled. The speed of response of the sensor 10 is proportional to the rate of adsorption of the aluminum oxide layer 14. This rate is greatest where the amount of adsorbed moisture potential is greatest.

Figure 3:
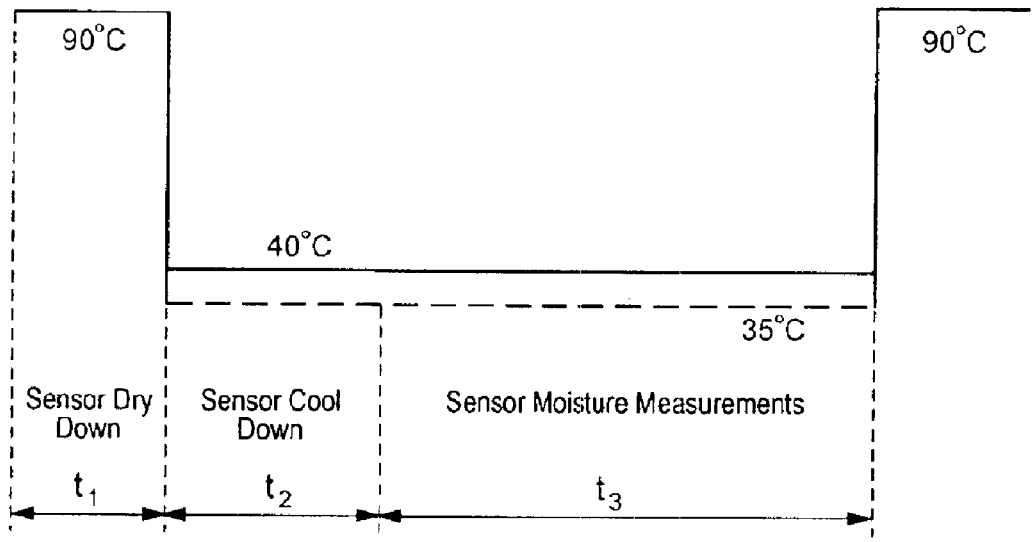
FIG. 3 diagrammatically illustrates the sensor conditioning and measurement cycle in accordance with the invention.

Turning to FIG. 3, a sensor conditioning and moisture measurement cycle is used to maximize this relationship. In the example given, the sensor 10 is heated to 90 Å° C., well above the sample gas temperature and held at that temperature for a time "t," of 15–30 seconds and preferably about 20 seconds, thus drying the sensor below the moisture concentration of the sample gas. The sensor is then allowed to cool down and stabilize for a second period of time "$t_2$" of from about 30 to about 50 seconds and preferably about 40 seconds. In the example shown, the sensor temperature is stabilized at, for example, 35 Å° C. The length of time required for cool down will vary inversely with the sample flow rate (the flow rate for the sample test was 700 sccm). Measurements are then taken at an optimized lower temperature (for example, 40 Å° C.) over a third time "$t_3$" of about 60–90 and preferably about 75 seconds. Unlike prior methodologies, measurements are taken only at this reduced or lower optimized temperature. This minimizes the effects of typically large sensor temperature coefficients. After the measurements have been taken, a new drying cycle is commenced.

During the measurement time period $t_3$, the rate of adsorption is determined by: 1) Taking 100 samples of sensor conductance.

2) Applying a 10-point moving average filter for noise reduction; and 3) Performing a linear regression on the filtered data, with the resulting slope (adsorption rate) used as a measure of sample moisture.

It will be appreciated that the temperature to which the sensor is heated and the temperature to which it is subsequently cooled, the time periods $t_1$, $t_2$ and $t_3$ as well as number of measurements collected may be adjusted to optimize sensor performance.

Figure 4:
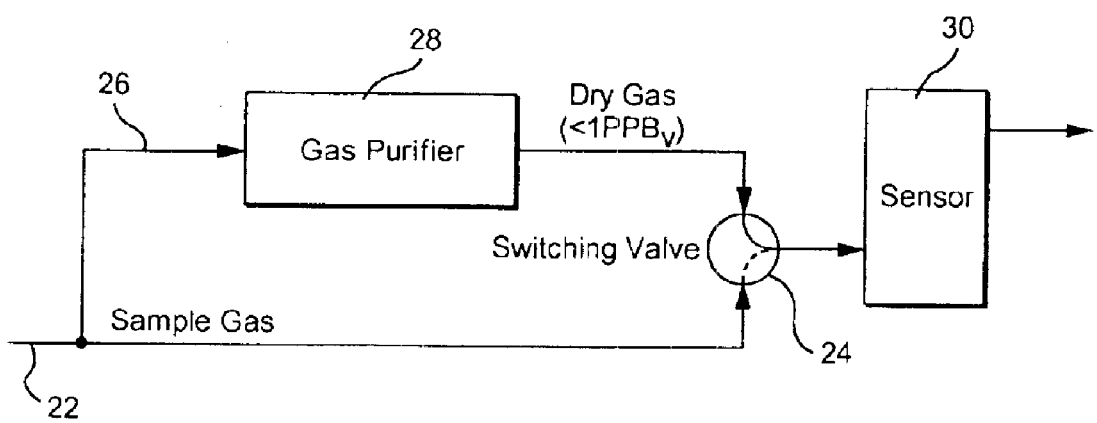
FIG. 4 diagrammatically illustrates another drying technique in accordance with the invention.

For sensors that do not incorporate a heater (or other means for controlling temperature), or if operation of the sensor at high temperatures is undesirable, other methods for drying the sensor may be employed. For example, with reference to FIG. 4, the flow of sample gas in line 22 may be halted and a dry gas with a moisture content of <1 PPM$_v$ may be temporarily introduced and diverted via valve 24 to stream 26 and gas purifier 28 before flowing through the sensor 30. The sensor 30 is exposed to the drying gas during the dry down cycle (time period $t_1$) and then the valve 24 is switched back to flow the sample gas to the sensor 30 during the measurement period. No cool down period is needed, but the drying time may have to be increased as this technique is less efficient than heating the sensor as described above.

Still another drying method involves using a Peltier device instead of a heater to control sensor temperature. This method has the advantage of more rapid sensor cool down. The major disadvantage, however, is that maximum drying temperature is limited by the Peltier device.

This novel methodology improves the response time of the sensor and minimizes if not eliminates the drift otherwise caused by large temperature coefficients.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of operating an aluminum oxide moisture sensor to measure moisture in a sample gas, where the sensor comprises a pair of electrodes sandwiched about a dielectric, the method comprising:

a) heating the sensor to a first temperature above the sample gas temperature and holding the sensor at said first temperature for a first predetermined period of time;

b) cooling down the sensor to a second lower temperature over a second predetermined period of time;

c) taking plural samples of sensor conductance over a third predetermined period of time at said lower temperature; and d) determining a rate of adsorption of the moisture and using the rate of adsorption as a measure of moisture in the sample gas.

2. The method of claim 1 wherein step c) is carried out by taking about 100 samples of sensor conductance over a period of between about 60 and 90 seconds.

3. The method of claim 2 wherein step d) is carried out in part by applying a 10-point moving average filter to said plural moisture samples to obtain data filtered for noise reduction.

4. The method of claim 1 wherein step d) is carried out in part by applying a 10-point moving average filter to said plural samples of sensor conductance to obtain data filtered for noise reduction.

5. The method of claim 1 wherein said first predetermined period of time is about 15–30 seconds.

6. The method of claim 5 wherein said first predetermined period of time is about 20 seconds.

7. The method of claim 1 wherein said second predetermined period of time is about 30–50 seconds.

8. The method of claim 7 wherein said second predetermined period of time is about 40 seconds.

9. The method of claim 1 wherein said third predetermined period of time is about 60–90 seconds.

10. The method of claim 9 wherein said third predetermined period of time is about 75 seconds.

11. The method of claim 1 wherein said first predetermined period of time is about 15–30 seconds; said second period of time is about 30–60 seconds; and said third period of time is about 60–90 seconds.

12. The method of claim 1 wherein step c) is carried out by taking about 100 samples of sensor conductance over a period of between about 60 and 90 seconds; and wherein step d) is carried out in part by applying a 10-point moving average filter to said 100 samples of sensor conductance to obtain data filtered for noise reduction.

13. The method of claim 1 wherein said first temperature is about 90° C. and said second lower temperature is about 35° C. to about 40° C.

14. A method of operating an aluminum oxide moisture sensor to measure moisture in a sample gas, where the sensor comprises a pair of electrodes sandwiched about a dielectric, the method comprising:

a) heating the sensor to a first temperature above the sample gas temperature and holding the sensor at said first temperature for a first predetermined period of time;

b) cooling down the sensor to a second lower temperature over a second predetermined period of time;

c) taking plural samples of sensor conductance over a third predetermined period of time at said lower temperature; and d) determining a rate of adsorption of the moisture and using the rate of adsorption as a measure of moisture in the sample gas;

wherein step d) is carried out in part by applying a 10-point moving average filter to said plural samples of sensor conductance to obtain data filtered for noise reduction, and by performing a linear regression on the data filtered for noise reduction to obtain a slope representative of the rate of adsorption.

15. A method of operating an aluminum oxide moisture sensor to measure moisture in a sample gas, where the sensor comprises a pair of electrodes sandwiched about a dielectric, the method comprising:

a) heating the sensor to a first temperature above the sample gas temperature and holding the sensor at said first temperature for a first predetermined period of time;

b) cooling down the sensor to a second lower temperature over a second predetermined period of time;

c) taking plural samples of sensor conductance over a third predetermined period of time at said lower temperature; and d) determining a rate of adsorption of the moisture and using the rate of adsorption as a measure of moisture in the sample gas;

wherein step c) is carried out by taking about 100 samples of sensor conductance over a period of between about 60 and 90 seconds;

wherein step d) is carried out in part by applying a 10-point moving average filter to said plural moisture samples to obtain data filtered for noise reduction and by performing a linear regression on the data filtered for noise reduction to obtain a slope representative of the rate of adsorption.

16. A method of operating an aluminum oxide moisture sensor to measure moisture in a sample gas, where the sensor comprises a pair of electrodes sandwiched about a dielectric, and the method comprising:

a) heating the sensor to a first temperature above the sample gas temperature and holding the sensor at said first temperature for a first predetermined period of time;

b) cooling down the sensor to a second lower temperature over a second predetermined period of time;

c) taking plural samples of sensor conductance over a third predetermined period of time at said second lower temperature; and d) determining a rate of adsorption of the moisture and using the rate of adsorption as a measure of moisture in the sample gas;

wherein step c) is carried out by taking about 100 samples of sensor conductance, and wherein said third predetermined period of time is about 60 and 90 seconds; and wherein step d) is carried out in part by applying a 10-point moving average filter to said plural samples of sensor conductance to obtain data filtered for noise reduction; and by performing a linear repression regression on the data filtered for noise reduction to obtain a slope representative of the rate of adsorption.

17. The method of claim 16 wherein said first predetermined period of time is about 15–30 seconds.

18. The method of claim 16 wherein said second period of time is about 30–60 seconds.

19. The method of claim 16 wherein said first predetermined period of time is 15–30 seconds; and said second predetermined period of time is 30–60 seconds.

20. The method of claim 16 wherein said third predetermined period of time is about 75 seconds.

21. The method of claim 20 wherein said first predetermined period of time is about 20 seconds and said second predetermined period of time is about 40 seconds.

22. The method of claim 16 wherein said first temperature is about 90° C. and said second lower temperature is about 35° C. to about 40° C.

* * * * *